United States Patent

Ochi et al.

Patent Number: 5,869,661
Date of Patent: Feb. 9, 1999

[54] METHOD OF PRODUCING A QUINOLONECARBOXYLIC ACID DERIVATIVE

[75] Inventors: Kiyoshige Ochi; Hirohito Shimizu, both of Tokyo, Japan

[73] Assignee: Chugai Seiyaku Kabushiki Kaisha, Tokyo, Japan

[21] Appl. No.: 339,404

[22] Filed: Nov. 17, 1994

Related U.S. Application Data

[63] Continuation of Ser. No. 185,989, filed as PCT/JP92/00901, Jul. 15, 1992, abandoned.

[30] Foreign Application Priority Data

Jul. 16, 1991 [JP] Japan ............................ 3-175547

[51] Int. Cl.$^6$ .................. C07D 215/56; C07D 295/155; C07D 291/04; C07D 265/28
[52] U.S. Cl. ......................... 544/128; 544/363; 546/156
[58] Field of Search .................... 544/363, 128; 546/156

[56] References Cited

U.S. PATENT DOCUMENTS 5,294,712  3/1994  Hermecz et al. ................. 544/363

FOREIGN PATENT DOCUMENTS 59-122470   7/1984   Japan .
62-252772  11/1987   Japan .
 8810253   12/1988   WIPO .

OTHER PUBLICATIONS

Miyamoto et al., Chem. Pharm. Bull. 38(9) p. 2472–2475 (1990).

*Primary Examiner*—Bernard Dentz
*Attorney, Agent, or Firm*—Browdy & Neimark

[57] ABSTRACT

The present invention is a method of producing a 6-fluoro-7-substituted quinolonecarboxylic acid derivative represented by the general formula (4):

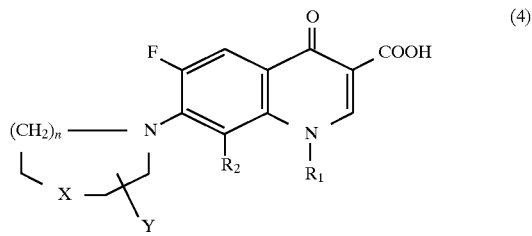

wherein the variables are defined in the specification, which is characterized by adding an alkylboric acid ester represented by the general formula (3):

$$B(OR_5)_3 \quad (3)$$

wherein $R_5$ represents a lower alkyl group, an aryl group, a substituted aryl group or a substituted aralkyl group to a 6-fluoroquinolonecarboxylic acid derivative represented by the general formula (1):

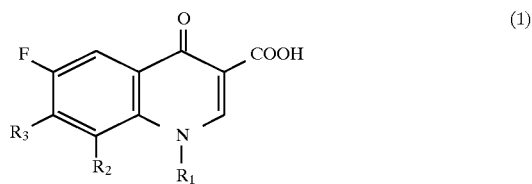

wherein $R_1$ and $R_2$ are as defined in the specification; and $R_3$ represents an optional, functional residue capable of participating in a nucleophilic substitution reaction, and a substituted saturated heterocyclic amine represented by the general formula (2):

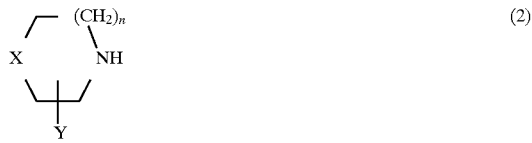

wherein X, Y and n are as defined in the specification, and condensing the reaction mixture with heating.

1 Claim, No Drawings

METHOD OF PRODUCING A QUINOLONECARBOXYLIC ACID DERIVATIVE

This application is a continuation of application Ser. No. 08/185,989, filed Jan. 13, 1994 now abandoned, which was a 371 of PCT/JP92/00901 filed Jul. 15, 1992.

TECHNICAL FIELD

The present invention relates to a novel method of producing a quinolonecarboxylic acid derivative represented by the following general formula (4):

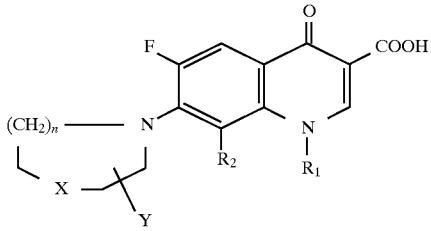

(4)

wherein $R_1$ represents a lower alkyl group or a cyclo lower alkyl group; $R_2$ represents a hydrogen atom, a halogen atom or a lower alkoxy group; X represents —$CH_2$—, —$NR_4$—, or —O—; $R_4$ represents a hydrogen atom or a lower alkyl group; Y represents a hydrogen atom, an amino group or a lower alkylamino group bonded to an optional carbon atom on a saturated heterocycle, or a group capable of easily being converted to said amino group or said lower alkylamino group according to a chemical means; and n represents 0 or 1.

BACKGROUND ART

The 6-fluoro-7-substituted quinolonecarboxylic acid derivative represented by the general formula (4) is a compound useful as a raw material of a medicine to be used as an anti-fungus agent and its synthesis intermediate.

Generally, as a method of producing said compound can be mentioned a method comprising introducing a specific substituent to the desired position of a benzene ring first and then forming a quinolone skeleton, and a method comprising introducing a substituent to be a specific precursor to a desired position first, forming a quinolone ring and then converting the substituent to be a precursor to a specific substituent.

In the case of the former, it lacks selectivity to introduce a specific substituent to a desired position and hence it has too many problems to be industrially useful. In the case of the latter, since the selectivity of a position and the reactivity in substitution increase due to the ring closure of a quinolone ring, it is relatively easy to introduce a specific substituent to a desired position.

In the following condensation reaction from the general formula (1) to the general formula (4), there have been difficulties for industrial production regarding the 7-alkylamination of introducing a specific substituent as below.

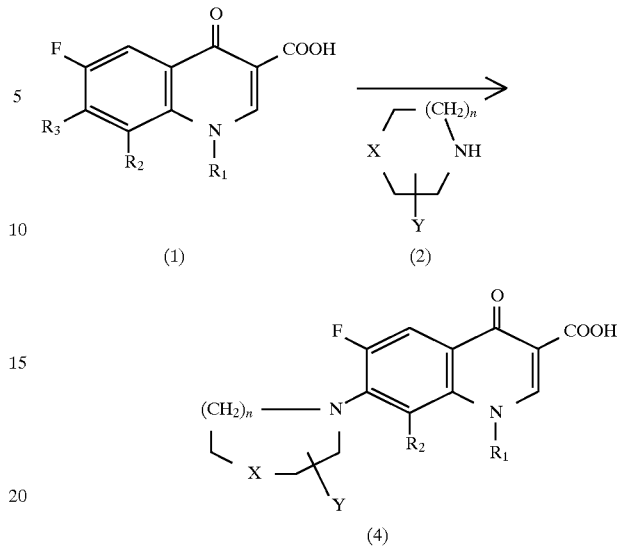

wherein $R_1$ represents a lower alkyl group or a cyclo lower alkyl group; $R_2$ represents a hydrogen atom, a halogen atom or a lower alkoxy group; $R_3$ represents an optional, functional residue capable of participating in a nucleophilic substitution; X represents —$CH_2$—, —$NR_4$— or —O—; $R_4$ represents a hydrogen atom or a lower alkyl group; Y represents a hydrogen atom, an amino group or a lower alkylamino group bonded to an optional carbon atom on a saturated heterocycle, or a group capable of easily being converted to an amino group or a lower alkylamino group according to a chemical means; and n represents 0 or 1.

Conventionally, the present reaction has obtained an objective compound by heating a compound represented by the general formula (1) and a compound represented by the general formula (2) in a solution (Japanese Patent Public Disclosure No. 252772/1987 and No. 16746/1989), or by converting a 3-position carboxyl group in the general formula (1) to borohydrofluoric acid ester with a view to making the nucleophilic substitution of the 7-position easy, then adding a compound represented by the general formula (2) and heating the reaction mixture in a solution (Japanese Patent Public Disclosure No. 316757/1988).

DISCLOSURE OF THE INVENTION

According to the former, however, reactivity increases since nucleophilicity varies according to the kinds of amines represented by the general formula (2), and a yield is generally low since the effects of a base to be added as a receptor of an acid forming according to the reaction are not large, which, as a result, has become a factor checking industrial scaling-up in the cost of production.

Though a method converting a 3-position carboxyl group to borohydrofluoric acid ester can obtain an objective compound at a relatively high yield, hydrofluoric acid occurring due to trifluoroborane to be used, the injuriousness of trifluoroborane itself to the human body, the corrosion of implements and equipment and wastes after reaction treatments have become factors checking industrial production. As a reaction process, it has a demerit that the operation is complicated due to esterification and deesterification.

The present inventors have engaged in assiduous studies with a view to dissolving the above-mentioned defects and as a result have found an effective catalyst for the nucleophilic substitution of the 7-position of a quinolone skeleton represented by the general formula (1), which has led to the accomplishment of the present invention.

The present invention is a method of producing a 6-fluoro-7-substituted quinolonecarboxylic acid derivative represented by the general formula (4):

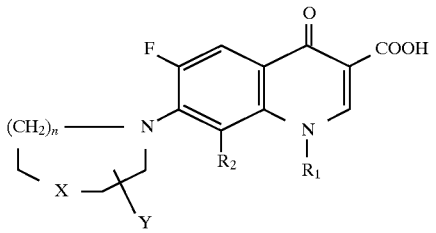

wherein $R_1$ represents a lower alkyl group or a cyclo lower alkyl group; $R_2$ represents a hydrogen atom, a halogen atom or a lower alkoxy group; X represents —$CH_2$—, —$NR_4$—, or —O—; $R_4$ represents a hydrogen atom or a lower alkyl group; Y represents a hydrogen atom, an amino group or a lower alkylamino group bonded to an optional carbon atom on a saturated heterocycle, or a group capable of easily being converted to said amino group or said lower alkylamino group according to a chemical means; and n represents 0 or 1, which is characterized by adding boric acid alkyl esters represented by the general formula (3):

$$B(OR_5)_3 \quad (3)$$

wherein $R_5$ represents a lower alkyl group, an aryl group, a substituted aryl group or a substituted aralkyl group to a 6-fluoroquinolonecarboxylic acid derivative represented by the general formula (1):

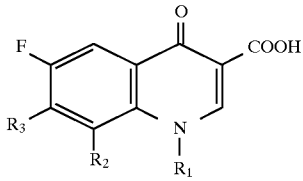

wherein $R_1$ and $R_2$ are as defined in the general formula (4); and $R_3$ represents an optional, functional residue capable of participating in a nucleophilic substitution reaction, and a substituted saturated heterocyclic amine represented by the general formula (2):

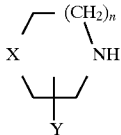

wherein X, Y and n are as defined in the general formula (4), and condensing the reaction mixture with heating in the absence of a solvent or in the presence of a solvent.

A compound represented by the general formula (1) being a raw material is derived from metafluorobenzoic acids represented by the general formula (5):

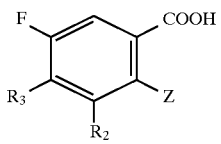

wherein $R_2$ and $R_3$ are as defined above; and Z represents a halogen atom, an $RSO_2$-group (wherein R represents a lower alkyl group, an aryl group or a substituted aryl group) or a hydroxyl group or esters thereof. Namely, in a reaction condensing to a quinolone ring represented by the general formula (1) using a compound represented by the general formula (5) as a raw material, Z represents a residue capable of constructing a quinolone ring by forming a C—N bond from carboxylic acid and a substituent Z with the structure of the general formula (5); specific examples thereof include fluorine, chlorine, bromine, iodine, a methane sulfonyl group, a benzenesulfonyl group, p-toluenesulfonyl group, a hydroxyl group or methyl esters and ethyl esters thereof.

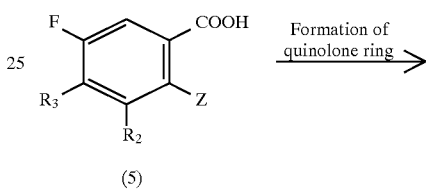

wherein $R_1$, $R_2$, $R_3$ and Z are as defined above.

In the performance of the nucleophilic substitution of a substituent $R_3$ of the general formula (1) and aliphatic amines represented by the general formula (2), amines represented by the general formula (2) represent saturated aliphatic heterocycles, for example, substituted or unsubstituted piperidines in case of X=$CH_2$, substituted or unsubstituted morpholines in case of X=O, and substituted or unsubstituted piperazines in case of X=$NR_4$, when n=1.

In such cases, $R_3$ represents an optional, functional residue capable of participating in a nucleophilic substitution and specific examples of the functional residue include fluorine, chlorine, bromine, iodine, a methane sulfonyl group, a benzenesulfonyl group and a p-toluenesulfonyl group.

Incidentally, in case of producing 6-fluoro-7-substituted quinolonecarboxylic acid ester represented by the general formula (4), it is preferable to use, for example, difluoroquinolonecarboxylic acid ester (DFQ-ester) represented by the general formula (1'), which is derived from trifluorobenzoic acid chloride represented by the general formula (5'), as a raw material instead of the compound of the general formula (5).

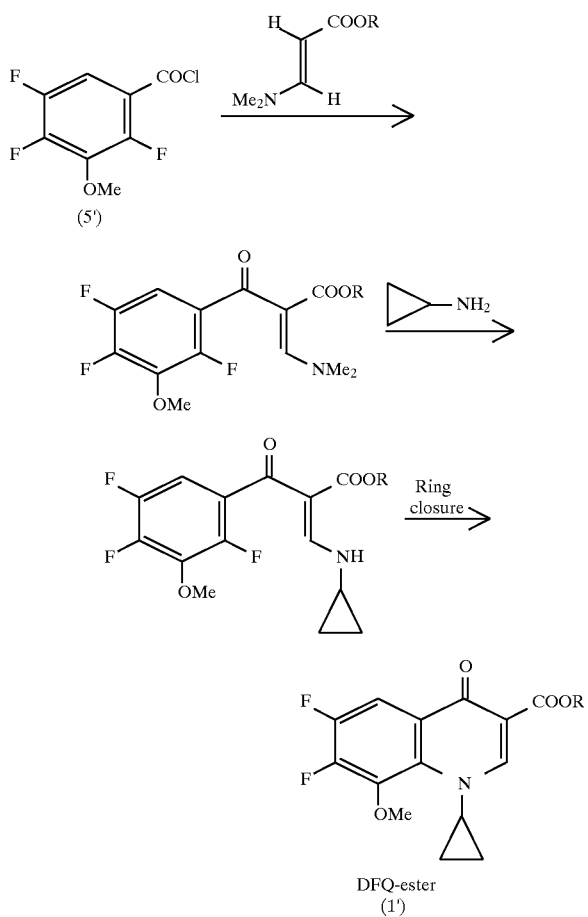

DFQ-ester
(1')

wherein R represents an alkyl group, an aryl group, a substituted aryl group, an aralkyl group or an substituted aralkyl group.

Regarding the position of Y bonding to a heterocycle, it is bonded as a carbon covalent bond at the 2-position or the 3-position in any case of $X=CH_2$, O or $NR_4$. Then, Y represents a hydrogen atom, an amino group or a lower alkylamino group.

Y may be a residue capable of being converted to an amino group or a lower alkylamino group according to an ordinary chemical means, for example, a nitro group, an acylamino group or a carbobenzyloxycarbonylamino group in addition to a hydrogen atom, an amino group or a lower alkylamino group. A nitro group can be easily converted to an amino group or a lower alkylamino group according to reduction, an acylamino group according to hydrolysis, and a carbobenzyloxycarbonylamino group according to reduction or hydrolysis. According to the present invention, Y may be a precursor in the performance of the nucleophilic substitution of the 7-position and converted to an amino group or a lower alkyl group according to reduction or hydrolysis after being converted to the compound of the general formula (4). Incidentally, a "lower alkyl group" in the present invention represents straight-chained or branched-chained one having carbon atoms of 1 to 5, and specifically represents a methyl group, an ethyl group, an n-propyl group, an n-butyl group and an n-pentyl group.

Boric acid alkyl ester to be used in the present invention is represented by the general formula (3):

$$B(OR_5)_3 \qquad (3)$$

wherein $R_5$ represents a lower alkyl group, an aryl group, a substituted aryl group, an aralkyl group or a substituted aralkyl group. Specific examples of $R_5$ include a methyl group, an ethyl group, an n-propyl group, an isopropyl group, an n-butyl group, a phenyl group, an o-tolyl group, a benzyl group and an o-methylphenethyl group.

Compounds represented by the general formula (3) are commercially available or they may be produced from boric acid and alcohols without separating as the general formula (3) in the present reaction system, and their forms for use are not particularly restricted.

Reaction solvents to be used in the present invention are not particularly restricted; a reaction may be carried out in the absence of a solvent, or preferable solvents are those that can dissolve raw materials, amines and boric acid alkyl ester with heating and raise a temperature to an optimum reaction temperature and do not decrease the activity as a Lewis acid catalyst. Preferably, by using lower aliphatic nitriles such as acetonitrile, propionitrile, butylonitrile and isobutylonitrile, a reaction can be carried out smoothly. An amount of boric acid alkyl ester to be added is in the range of 0.5 to 2 mols based on the compound represented by the general formula (1), preferably at the equivalent mol.

Regarding a reaction temperature, optimum conditions can be selected according to the kinds of raw materials, amines and boric acid alkyl ester; preferably a reaction is generally performed under heating taking the boiling points of a solvent and boric acid alkyl ester to be added into consideration. Particularly preferably, a reaction is performed at a temperature around 100° C. for several hours.

The objective 7-substituted quinolonecarboxylic acid derivative represented by the general formula (4) can be obtained at a high yield by condensing a reaction mixture, adding water or an organic solvent therein and adjusting a pH.

According to the method of the present invention, said compound, which has had a low yield and many problems in the aspect of safety, can be produced safely at a high yield as industrial mass production.

EXAMPLES

Hereunder, Examples of the method of the present invention will be described, but the present invention is restricted by these Examples by no means.

Example 1

Synthesis of 1-cyclopropyl-6-fluoro-1,4-dihydro-8-methoxy-4-oxo-7-(1-pyrazinyl)-3-quinolinecarboxylic acid A mixture of 1.48 g of 1-cyclopropyl-6,7-difluoro-1,4-dihydro-8-methoxy-4-oxo-3-quinolinecarboxylic acid (5 mmol), 0.86 g of anhydrous piperazine (10 mmol), 1.04 g of trimethoxyborane (10 mmol) and 7.5 ml of acetonitrile was refluxed with heating for 4 hours. The reaction solution was cooled to room temperature, 20 ml of water was added therein, a pH was adjusted to 8 with 6N—HCl, and separated crystals were filtered and dried to obtain 1.46 g of the objective compound.

Melting point: 174.0°–177.0° C.

NMR spectrum (DMSO): 8.795(s,1H), 7.731(d,J=12.5 Hz,1H), 4.05–4.15(m,1H), 3.771(s,3H), 2.8–3.0(m,4H), 1.0–1.2(m,4H)

Example 2

Synthesis of 1-cyclopropyl-6-fluoro-1,4-dihydro-8-methoxy-4-oxo-7-(1-pyperidinyl)-3-quinolinecarboxylic acid A mixture of 1.48 g of 1-cyclopropyl-6,7-difluoro-1,4-dihydro-8-methoxy-4-oxo-3-quinolinecarboxylic acid (5 mmol), 0.85 g of piperidine (10 mmol), 1.04 g of trimethoxyborane (10 mmol) and 7.5 ml of acetonitrile was refluxed with heating for 4 hours. The reaction solution was cooled to room temperature, 20 ml of water was added therein, and separated crystals were filtered and dried to obtain 1.44 g of the objective compound.

Melting point: 219.5°–220.5° C.

NMR spectrum (CDCl$_3$): 14.961(s,1H), 8.690(s,1H), 7.772(d,J=10.89 Hz,1H), 4.0–4.2(m,1H), 3.760 (s,3H), 2.5–2.7(m,4H), 1.6–1.8(m,6H), 1.0–1.2(m,4H)

Example 3

Synthesis of 1-cyclopropyl-6-fluoro-1,4-dihydro-8-methoxy-4-oxo-7-(morpholino)-3-quinolinecarboxylic acid A mixture of 1.48 g of 1-cyclopropyl-6,7-difluoro-1,4-dihydro-8-methoxy-4-oxo-3-quinolinecarboxylic acid (5 mmol), 0.85 g of morpholine (10 mmol), 1.04 g of trimethoxyborane (10 mmol) and 7.5 ml of acetonitrile was refluxed with heating for 4 hours. The reaction solution was cooled to room temperature, 20 ml of water was added therein, a pH was adjusted to 8 with 6N—HCl, and separated crystals were filtered and dried to obtain 1.30 g of the objective compound.

Melting point: 210.0° C. (decomposition)

NMR spectrum (CDCl$_3$): 14.885(s,1H), 8.706(s,1H), 7.753(d,J=12.54 Hz,1H), 4.0–4.2(m,1H), 3.806(s,3H), 3.3–3.4(m,4H), 2.5–2.6(m,4H), 1.0–1.2(m,4H)

Example 4

Synthesis of 1-ethyl-6-fluoro-1,4-dihydro-8-methoxy-4-oxo-7-(1-piperazinyl)-3-quinolinecarboxylic acid A mixture of 2.83 g of 1-ethyl-6,7-difluoro-1,4-dihydro-8-methoxy-4-oxo-3-quinolinecarboxylic acid (10 mmol), 1.72 g of anhydrous piperazine (20 mmol), 1.04 g of trimethoxyborane (10 mmol) and 15 ml of acetonitrile was refluxed with heating for 4.5 hours. The reaction solution was cooled to room temperature, 30 ml of water was added therein, and separated crystals were filtered and dried to obtain 2.00 g of the objective compound.

Melting point: 169.0° C.

NMR spectrum (DMSO): 8.885(s,1H), 7.818(d,J=11.54 Hz,1H), 4.686(q,J=6.6 Hz,2H), 3.2–3.4(m,4H), 2.8–3.0(m, 4H), 1.315(t,J=52 Hz,3H)

Example 5

Synthesis of 1-ethyl-6-fluoro-1,4-dihydro-8-methoxy-4-oxo-7-(1-piperidinyl)-3-quinolinecarboxylic acid A mixture of 2.83 g of 1-ethyl-6,7-difluoro-1,4-dihydro-8-methoxy-4-oxo-3-quinolinecarboxylic acid (10 mmol), 1.70 g of piperidine (20 mmol), 1.04 g of trimethoxyborane (10 mmol) and 15 ml of acetonitrile was refluxed with heating for 4.5 hours. The reaction solution was cooled to room temperature, 30 ml of water was added therein, a pH was adjusted to 8 with 6N—HCl, and separated crystals were filtered and dried to obtain 2.20 g of the objective compound.

Melting point: 177.0°–179.0° C.

NMR spectrum (CDCl$_3$): 14.963(s,1H), 8.548(s,1H), 7.834(d,J=12.2 Hz,1H), 4.531(q,J=7.26 Hz,2H), 3.2–3.4(m, 4H), 1.6–1.8(m,6H), 1.391(t,J=6.93 Hz,3H)

Example 6

Synthesis of 1-cyclopropyl-6-fluoro-1,4-dihydro-8-methoxy-4-oxo-7-(1-methylaminopiperidin-1-yl)-3-quinolinecarboxylic acid using (iPrO)$_3$B A mixture of 2.95 g of 1-cyclopropyl-6,7-difluoro-1,4-dihydro-8-methoxy-4-oxo-3-quinolinecarboxylic acid (10 mmol), 3.75 g of 3-methylaminopiperidine 2HCl (20 mmol), 3.75 g of (iPrO)$_3$B (20 mmol), 4.4 g of triethylamine (43 mmol) and 20 ml of acetonitrile was refluxed with heating for 6 hours. The reaction solution was cooled to room temperature, 20 ml of water was added therein, and separated crystals were filtered and dried to obtain 1.80 g (46.3%) of the objective compound.

Example 7

Synthesis of 1-cyclopropyl-6-fluoro-1,4-dihydro-8-methoxy-4-oxo-7-(3-methylaminopiperidin-1-yl)-3-quinolinecarboxylic acid using (PhO)$_3$B A mixture of 2.95 g of 1-cyclopropyl-6,7-difluoro-1,4-dihydro-8-methoxy-4-oxo-3-quinolinecarboxylic acid (10 mmol), 3.75 g of 3-methylaminopiperidine 2HCl (20 mmol), 5.80 g of (PhO)$_3$B (20 mmol), 4.4 g of triethylamine (43 mmol) and 20 ml of acetonitrile was refluxed with heating for 6 hours. The reaction solution was cooled to room temperature, made acid with 6N—HCl and extracted with 10 ml of ethyl acetate twice. The pH of the water layer was adjusted to 8 to 9 with 25% NaOH, and separated crystals were filtered and dried to obtain 1.90 g (48.8%) of the objective compound.

Example 8

Synthesis of 1-cyclopropyl-6-fluoro-1,4-dihydro-8-methoxy-4-oxo-7-pyrrolidino-3-quinolinecarboxylic acid A mixture of 2.95 g of 1-cyclopropyl-6,7-difluoro-1,4-dihydro-8-methoxy-4-oxo-3-quinolinecarboxylic acid (10 mmol), 1.42 g of pyrrolidine (20 mmol), 1.04 g of trimethoxyborane (10 mmol) and 20 ml of acetonitrile was refluxed with heating for 3.5 hours. The reaction solution was cooled to room temperature, acetonitrile was distilled under vacuum and 15 ml of ethanol was added into the resultant product. Separated crystals were filtered and dried to obtain 3.05 g of the objective compound (88.2%).

Melting point: 257.0°–258.0° C.

NMR spectrum (CDCl$_3$): 15.095(s,1H), 8.768(s,1H), 7.790(d,J=13.86 Hz,1H), 4.0–4.1(m,1H), 3.538(s,3H), 3.5–3.7(m,4H), 1.8–2.0(m,4H), 1.0–1.2 (m, 4H)

Example 9

Synthesis of 1-cyclopropyl-6-fluoro-1,4-dihydro-8-methoxy-4-oxo-7-[3-(N-acetyl-N-methylamino) pyrrolidino]pyrrolidino-3-quinolinecarboxylic acid A mixture of 2.95 g of 1-cyclopropyl-6,7-difluoro-1,4-dihydro-8-methoxy-4-oxo-3-quinolinecarboxylic acid (10 mmol), 2.84 g of 3-(N-acetyl-N-methylamino)pyrrolidine (20 mmol), 1.04 g of trimethoxyborane (10 mmol) and 20 ml of acetonitrile was refluxed with heating for 3.5 hours. The reaction solution was cooled to room temperature, acetonitrile was distilled under vacuum and 15 ml of ethanol was added into the resultant product. Separated crystals were filtered and dried to obtain 3.50 g of the objective compound (83.9%).

Melting point: 206.0°–207.0° C.

NMR spectrum (CDCl₃): 14.394(s,1H), 8.786(s,1H), 7.801(d,J=13.53 Hz,1H), 5.3–5.4(m,1H), 3.5–4.0(m,5H), 3.032(s,1H), 2.160(s,3H), 2.0–2.3(m,3H), 0.9–1.3(m,4H)

REFERENTIAL EXAMPLES

Referential Example 1

Synthesis of DFQ-benzyl ester

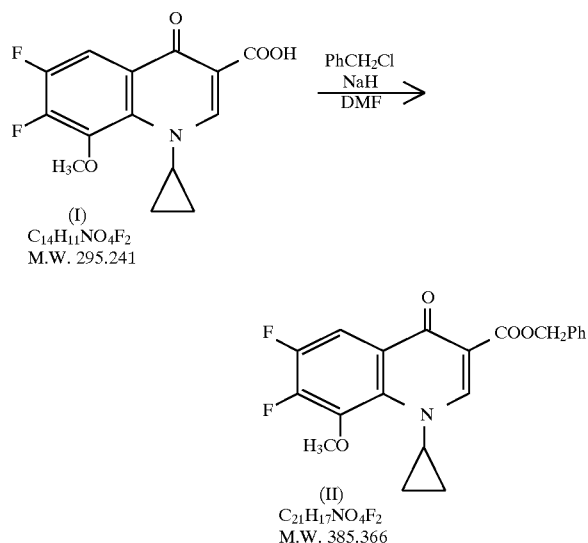

NaH (2.6 g, 0.065 mol) was suspended and dissolved into DMF (dimethylformamide; 25 ml) and the reaction solution was stirred for about 10 minutes. A DMF solution (100 ml) of 1-cyclopropyl-6,7-difluoro-1,4-dihydro-8-methoxy-4-oxo-3-quinolinecarboxylic acid (I) (14 g, 0.047 mol) was slowly dropped therein. After the completion of adding, the reaction mixture was stirred at room temperature for about 10 minutes and further PhCH₂Cl (benzylchloride; 6.0 ml, 0.052 mol) was dropped therein. The reaction mixture was heated on an oil bath at 100° C. for 6 hours. After the completion of heating, the reaction mixture was poured into water (500 ml) slowly to separate crystals. Separated crystals were washed with water three times and then with MeOH to obtain 1-cyclopropyl-6,7-difluoro-1,4-dihydro-8-methoxy-4-oxo-3-quinolinecarboxylic acid benzyl ester (II) (13.6 g, yield: 74%).

NMR spectrum (δ):

1.02–1.26 (4H, m, C$\underline{H}_2$—C$\underline{H}_2$)

3.92–3.99 (1H, m, C$\underline{H}$—)

| 4.08 | (3H,s, —OC$\underline{H}_3$) |
| 5.39 | (2H,s, —C$\underline{H}_2$Ph) |
| 7.31–7.52 | (5H,m, —Ph) |
| 8.02–8.08 | (1H,dd, C$_5$—H) |
| 8.61 | (1H,s, C$_2$—H) |

Referential Example 2

Synthesis of 1-cyclopropyl-6-fluoro-1,4-dihydro-8-methoxy-4-oxo-7-(3-methylaminopiperidin-1-yl)-3-quinolinecarboxylic acid benzyl

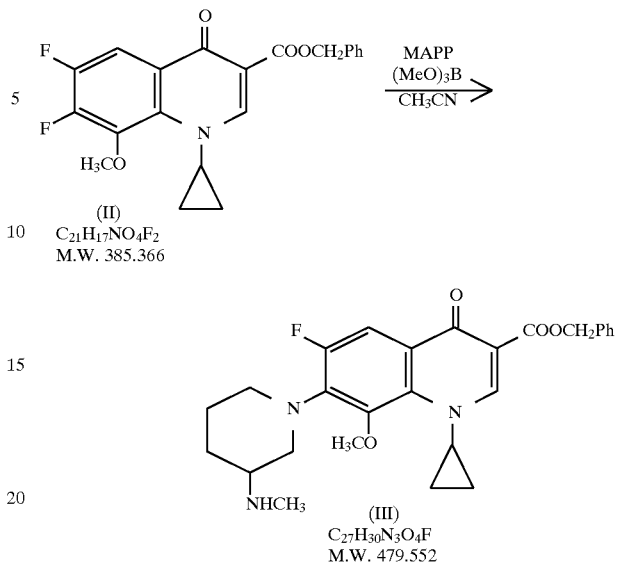

DFQ benzyl ester (II) (1.0 g, 0.026 mol) obtained in Referential Example 1 was suspended into acetonitrile (5 ml) and dissolved uniformly by heating the reaction mixture at a temperature of 40° to 50° C. on an oil bath. After trimethoxyborane (0.54 g, 0.052 mol) was dropped therein and the resultant mixture was stirred for about 10 minutes, 3-methylaminopiperidine (1.19 g, 0.010 mol) suspended in acetonitrile (5 ml) was added therein and the reaction mixture was refluxed with heating on an oil bath for 5 hours. The whole was poured into water, extracted with ethyl acetate and the ethyl acetate layer was washed with a saturated saline salt solution. The resultant product was dried over anhydrous MgSO₄, and separated and purified according to silica gel chromatography (5% MeOH—CHCl₃) to obtain the objective compound (III) (0.10 g, yield: 8%).

NMR spectrum (δ):

0.86–1.26 (4H, m, C$\underline{H}_2$—C$\underline{H}_2$)

1.78–2.27 (4H, m, piperidine CH₂, NHCH₃)

2.78 (3H,s, NHC$\underline{H}_3$)

3.12–3.44 (6H, s, piperidine)

3.69 (3H,s, —OC$\underline{H}_3$)

3.85–3.90 (1H, m, C$\underline{H}$—)

| 5.32 | (2H,s, C$\underline{H}_2$—Ph) |
| 7.31–7.47 | (5H,m, —Ph) |
| 7.78–7.83 | (1H,d, C$_5$—H) |
| 8.59 | (1H,s, C$_2$—H) |

INDUSTRIAL UTILIZATION

When 6-fluoro-7-substituent-3-quinolonecarboxylic acid is produced according to a conventional method, the cost of production is high due to a low yield; in the case of a relatively high yield, hydrofluoric acid and trifluoroborane occur, which are harmful to the human body and implements and equipment and besides cause environmental pollution, and hence it has been unsuitable for industrial production.

According to the method of the present invention producing 6-fluoro-7-substituent-3-quinolonecarboxylic acid using alkylboric acid esters as a catalyst, the defects of conventional methods have been dissolved and a method of producing economically 6-fluoro-7-substituent-3-quinolonecarboxylic acid at a relatively high yield without forming harmful substances has been established. The method of the present invention is extremely useful as a method of industrial production.

We claim:

1. A method of producing a 6-fluoro-7-substituted quinolonecarboxylic acid derivative represented by the general formula (4):

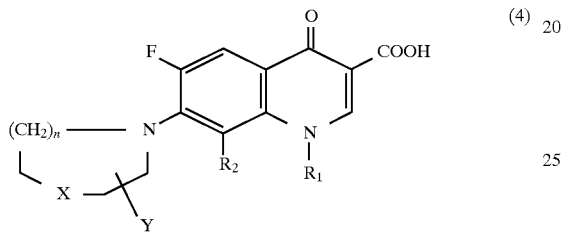

(4)

wherein $R_1$ represents a lower alkyl group or a cyclo lower alkyl group; $R_2$ represents a hydrogen atom, a halogen atom or a lower alkoxy group; X represents $-CH_2-$, $-NR_4-$ or $-O-$; $R_4$ represents a hydrogen atom or a lower alkyl group; Y represents a hydrogen atom, or an amino group or a lower alkylamino group bonded to an optional carbon atom on a saturated heterocycle, or a group capable of easily being converted to said amino group or said lower alkylamino group according to a chemical means; and n represents 0 or 1, which is characterized by adding an alkylboric acid ester represented by the general formula (3):

$$B(OR_5)_3 \quad (3)$$

wherein $R_5$ represents a lower alkyl group, an aryl group, a substituted aryl group or a substituted aralkyl group to a 6-fluoroquinolonecarboxylic acid derivative represented by the general formula (1):

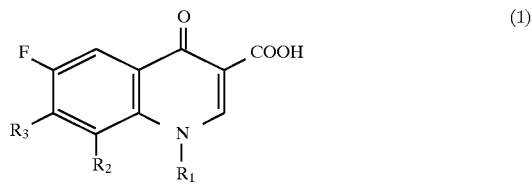

(1)

wherein $R_1$ and $R_2$ are as defined in the general formula (4); and $R_3$ represents an optional, functional residue capable of participating in a nucleophilic substitution reaction, and a substituted saturated heterocyclic amine represented by the general formula (2):

(2)

wherein X, Y and n are as defined in the general formula (4), and condensing the reaction mixture with heating in the absence of a solvent or in the presence of a solvent.

* * * * *